(12) United States Patent
de Franca Teixeira dos Prazeres et al.

(10) Patent No.: US 7,169,917 B2
(45) Date of Patent: Jan. 30, 2007

(54) PURIFICATION OF PLASMID DNA BY HYDROPHOBIC INTERACTION CHROMATOGRAPHY

(75) Inventors: Duarte Miguel de Franca Teixeira dos Prazeres, Lisbon (PT); Maria Margarida Fonseca Rodrigues Diogo, Lisbon (PT); Joao Antonio De Sampaio Rodrigues Queiroz, Covilha (PT)

(73) Assignees: Instituto Superior Tecnico, Lisbon (PT); Universidade da Beira Interior, Covilha (PT)

( * ) Notice: Subject to any disclaimer, the term of this patent is extended or adjusted under 35 U.S.C. 154(b) by 283 days.

(21) Appl. No.: 10/332,633

(22) PCT Filed: Jul. 6, 2001

(86) PCT No.: PCT/PT01/00012

§ 371 (c)(1),
(2), (4) Date: Jun. 23, 2003

(87) PCT Pub. No.: WO02/04027

PCT Pub. Date: Jan. 17, 2002

(65) Prior Publication Data

US 2004/0038393 A1 Feb. 26, 2004

(30) Foreign Application Priority Data

Jul. 10, 2000 (PT) .................................. 102491

(51) Int. Cl.
C07H 21/04 (2006.01)
(52) U.S. Cl. ..................... 536/25.4; 210/635
(58) Field of Classification Search ............... 536/25.4; 210/635
See application file for complete search history.

(56) References Cited

U.S. PATENT DOCUMENTS 5,561,064 A * 10/1996 Marquet et al. ......... 435/320.1
5,707,812 A    1/1998 Horn et al.
6,503,738 B1 * 1/2003 Thatcher et al. ............ 435/91.1

FOREIGN PATENT DOCUMENTS

WO    WO009851693    * 11/1998

OTHER PUBLICATIONS

Diogo M M et al. "Purification of a cystic fibrosis plasmid vector for gene therapy using hydrophobic interaction chromatography." Biotechnology and Bioengineering, vol. 68 No. 5, Jun. 5, 2000, pp. 576-583.

Diogo M M et al. "Separation and analysis of plasmid denatured forms using hydrophobic interation chromatography." Analytical Biochemistry., vol. 275, No. 1, Nov. 1, 1999, pp. 122-124.

Birnboim et al., Nucleic Acids Research, vol. 7, No. 6, 1979; *A Rapid Alkaline Extraction Procedure for Screening Recombinant Plasmid DNA* 1513-1523, © Information Retrieval Limited.

Ferreira et al., Centre for Biological and Chemical Engineering, Instituto Superior Tenico, Portugal; *Monitoring of Process Streams in the Large-scale Production and Purification of Plasmid DNA for Gene Therapy Applications;* © 1999 Pharm. Pharmacol. Commun., 5: 57-59.

Ferreira et al.; Centro de Engenhaira Biologica e Quimica, Instituto Superior Tecnico, Portugal; *Development of Process Flow Sheets for the Purification of Supercoiled Plasmids for Gene Therapy Applications;* Biotechnol. Prog. 1999, 15, 725-731.

Green et al.; BioPharm 1997; *Preparative Purification of Supercoiled Plasmid DNA Therapeutic Applications;* 52-62.

Horn et al.; Mary Ann Liebert, Inc.; *Cancer Gene Therapy Using Plasmid DNA: Purification of DNA for Human Clinical Trials;* Human Gene Therapy 6:565-573 (May 1995).

Prazeres et al.; Elsevier Science B.V.; *Preparative Purification of Supercoiled Plasmid DNA using Anion-exchange Chromatography;* Journal of Chromatography A, 806, © 1998, 31-45.

Prazers et al.; TIBTECH Apr. 1999 (vol. 17); *Large-scale Production of Pharmaceutical-grade Plasmid DNA for Gene Therapy: Problems and Bottlenecks;* © 1888 Elsevier Science: 169-174.

Queiroz et al.; Elsevier Science B.V.; *Hydrophobic Interaction Chromatography of Chromobacterium viscosum Lipase;* Journal of Chromatography A, 707, © 1995, 137-142.

Queiroz et al.; Elsevier Science B.V.; *Hydrophobic Interaction Chromatography of Chromobacterium viscosum Lipase on Polyethylene Glycol Immobilized on Sepharose;* Journal of Chromatography A, 734, © 1996, 213-219.

Sambrook et al.; Laboratory Manual: *Molecular Cloning;* Cold Spring Harbor Laboratory Press; © 1989, front cover page, reverse front cover page, section: *Extraction and Purification of Plasmid DNA:* pp. 1.21-1.52; Reference pp. 1.105-1.110.

(Continued)

*Primary Examiner*—James Ketter
(74) *Attorney, Agent, or Firm*—Merchant & Gould P.C.

(57) ABSTRACT

The invention refers to a new process for the production of purification of high purity plasmid DNA. The process comprehends: a) the production of cells containing plasmid DNA, b) the disruption of the cells in order to obtain a lysate containing plasmid DNA, c) a concentration step by precipitation with isopropanol, d) a pre-purification and conditioning step by the addition of ammonium sulphate, e) a purification step using hydrophobic interaction chromatography, f) a final concentration and/or buffer exchange step. The process is scaleable, it does not use enzymes or mutagenic agents and it enables the preparation of plasmid DNA with pharmaceutical grade, which complies with the requirements of regulatory agencies. The invention belongs to the technical domain of Biochemical Engineering/Biotechnology.

15 Claims, 5 Drawing Sheets

OTHER PUBLICATIONS

Schleef, Martin (reprint); Second, Completely Revised Edition © 1999; *Biotechnology;* vol. 5a: Recombinant Proteins, Monoclonal Antibodies and Therapeutic Genes; Wiley-VCH; front cover page, table of contents page; 20 Issues of Large-Scale Plasmid DNA Manufacturing; article front cover page, pp. 444-469.

Schluep et al.; Nucleic Acids Research; *Purification of Plasmids by Triplex Affinity Interaction;* © 1998 Oxford University Press; pp. 4524-4528.

Sundberg et al.; Journal of Chromatography, 90 (1974); *Preparation of Adsorbents for Biospecific Affinity Chromatography;* © Elsevier Scientific Publishing Company, pp. 87-98.

U.S. Department of Health and Human Services, Food and Drug Administration, Center for Biologics Evaluation and Research, Mar. 1998; *Guidance for Industry; Guidance for Human Somatic Cell Therapy and Gene Therapy;* front cover page, table of contents pp. i and ii; pp. 1-27.

\* cited by examiner

US 7,169,917 B2

PURIFICATION OF PLASMID DNA BY HYDROPHOBIC INTERACTION CHROMATOGRAPHY

FIELD OF THE INVENTION

The invention refers to a process for the production and purification of high purity plasmid DNA. The proposed method enables the preparation of considerable amounts (milligrams, grams) of plasmid DNA with pharmaceutical grade for use in gene therapy and DNA vaccination. The invention belongs to the technical domain of Biochemical Engineering/Biotechnology.

BACKGROUND OF THE INVENTION

Recent studies have demonstrated that plasmid DNA can be used as a non-viral vector to deliver therapeutic genes to human cells and tissues as a way of curing and preventing diseases such as cystic fibrosis and AIDS. One of the technological challenges associated with gene therapy and DNA vaccination is the development of processes for the large-scale purification of plasmid DNA, capable of delivering a product that is safe, efficient and economic according to the requirements of regulatory agencies. Although plasmid DNA is produced by growing bacterial cells like the majority of recombinant proteins, the information relative to purification methods for their large-scale production is still scarce. Additionally, the existent laboratory-scale protocols are not adequate for the large-scale production of pharmaceutical grade plasmid DNA, due to technological, economic and safety reasons, since they use organic, mutagenic and toxic compounds (phenol, chloroform, ethidium bromide, cesium chloride) and animal derived enzymes (lysozyme, protease K and RNase). The use of these reagents in a process for the production of a product that is intended for human use always requires its complete removal from the end product. This removal then has to be demonstrated unequivocally by the manufacturer, a process that is often difficult to carry out. The use of some reagents may even be barred in the first place. Some plasmid purification processes have been developed on the basis of these laboratory protocols with the intention of producing a pharmaceutical-grade product at large-scale.

The challenge posed to the purification process is the removal of impurities such as lipopolysaccharides, RNA, denatured plasmid DNA and genomic DNA (gDNA), which have properties similar to those of plasmid DNA and which behave identically in most of the purification operations. The production and purification of plasmid DNA comprehends the usual steps of fermentation, primary isolation and purification. At laboratory scale, primary isolation is usually performed by the alkaline lysis method, developed to disrupt cells and denature genomic DNA and proteins that precipitate together with cellular debris and other impurities. At this stage the use of animal-derived enzymes such as lysozyme and RNase is common. Due to its animal origin, these components may introduce viral (or other) contamination in the product, and thus its use is not advisable.

The lysate obtained may be concentrated and partially purified using extraction with organic solvents (mixtures of phenol, chloroform and iso-amylic alcohol) and/or precipitation with adequate agents such as isopropanol, ethanol, poly(ethylene glycol) and ammonium acetate. One or two chromatography operations usually follow. In most cases anion exchange and gel filtration chromatography have been used; affinity and reversed phase chromatography applications have also been described. On the other hand, hydrophobic interaction chromatography, which is a powerful technique often used in the purification of therapeutic proteins, has not been used for the purification of plasmid DNA.

DESCRIPTION OF THE INVENTION

Figure 1:
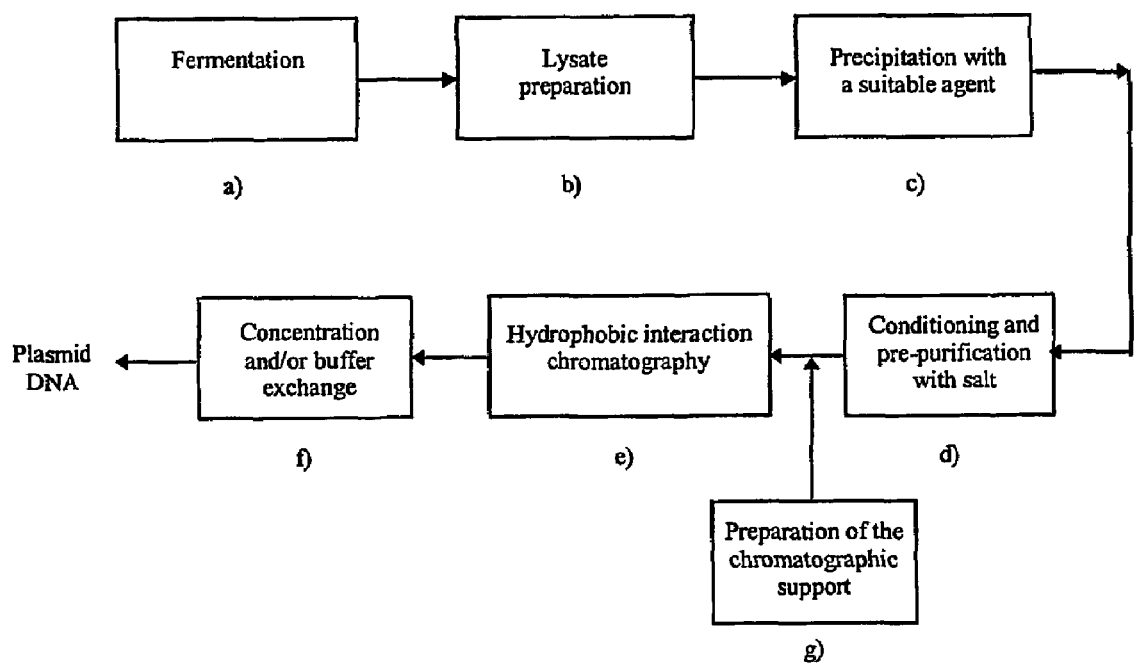
FIG. 1 is a schematic showing a process for the purification and production of plasmid DNA.

The invention refers to a new process, which is adequate for the production and purification of plasmid DNA for use in gene therapy and DNA vaccination. This process is scaleable. The main step consists in the use of hydrophobic interaction chromatography. The process, which is described next for the case of plasmid DNA hosted in an $E.\ coli$ strain and schematised in FIG. 1 comprehends:
a) the production of cells containing plasmid DNA by fermentation
b) the disruption of the cells in order to obtain a lysate containing plasmid DNA
c) a precipitation step with an adequate agent designed to concentrate the plasmid DNA
d) a pre-purification and conditioning step accomplished by the addition of a salt
e) a purification step using hydrophobic interaction chromatography
f) a final concentration and/or buffer exchange step
g) the invention also describes the preparation of some non-commercial hydrophobic interaction chromatography supports which are suited for the purification of plasmid DNA.

The different steps are described next in more detail.
a) Production of cells: cells containing the plasmid DNA are grown as usual, in shake flask or fermentor, using an adequate culture medium and suitable conditions of temperature and pH. The cells are harvested as usual by centrifugation or microfiltration and used immediately or else frozen for later processing.
b) Preparation of the lysate: the cells obtained in a) are re-suspended in a buffer with a composition (e.g. sodium acetate, potassium citrate), pH and ionic strength adequate to the subsequent lysis step. The lysis is designed to disrupt the cells, extract plasmid DNA and precipitate proteins, genomic DNA and high molecular weight RNA. The lysis may be mechanical (e.g. in a sonicator, high-pressure homogenizer or French press) or chemical (e.g. alkaline lysis). In the preferred case of a chemical lysis in an alkaline medium, an alkali (e.g. sodium hydroxide, potassium hydroxide) and detergent (e.g. Tween® 80 or sodium dodecyl sulphate) solution with an adequate composition and ionic strength is added slowly to the cell suspension. The pH of the resulting mixture must be controlled between 12 and 12.5, in order to minimise denaturation of plasmid DNA. The lysis mixture is then neutralised by slowly adding a salt solution with an adequate pH (e.g. 3 M potassium acetate, pH 5.5) in order to facilitate the removal of insoluble material resulting from lysis. This insoluble material is removed by centrifugation and/or filtration with filters, using adequate conditions. Filtrating agents or aids may be used to improve the efficiency of the process. The outcome of this step is a clarified lysate containing plasmid DNA and cell impurities (RNA, denatured genomic DNA, proteins, lipopolysaccharides).

c) Concentration by precipitation: the plasmid DNA contained in the clarified lysate is precipitated by the addition of an agent such as isopropanol, ethanol or poly(ethylene glycol) under adequate concentration and conditions. The precipitate obtained is recovered as usual, by centrifugation or filtration, and re-dissolved in a smaller volume of an adequate buffer.

d) Pre-purification and conditioning: the plasmid DNA obtained in c) is pre-purified and conditioned by addition of an adequate salt. The addition of the salt enables not only the precipitation of the majority of the proteins (more than 95%) remaining in the lysate, but also creates the adequate conditions of composition and ionic strength for the subsequent step of hydrophobic interaction chromatography. Typically a salt such as ammonium acetate, sodium acetate, ammonium or sodium sulphate will be added in high concentration (1.5–3.0 M). The resulting precipitate is removed using adequate techniques such as centrifugation and filtration. The obtained supernatant is rich in plasmid DNA but also contains impurities such as proteins, genomic DNA, RNA, oligonucleotides and lipopolysaccharides. According to the invention, the subsequent purification is performed by hydrophobic interaction chromatography using an adequate solid support.

e) Hydrophobic interaction chromatography: the type of chromatography proposed here (hydrophobic interaction) explores differences in hydrofobicity between the plasmid DNA and impurity molecules. Specifically, it explores the higher hydrophobicity of single stranded nucleic acids, which account for most of the impurities (RNA, oligonucleotides, denatured genomic DNA and plasmid DNA), comparatively to double stranded nucleic acids such as is the case of the target product, plasmid DNA. Lipopolysaccharides (LPS) are another class of impurities that are more hydrophobic than plasmid DNA, due to the presence of a lipidic part (lipid A) in their molecular structure. The support for hydrophobic interaction chromatography may be a commercial one or not. According to the method, the referred support is packed in a column with dimensions chosen on the basis of the scale of the process. An adequate volume of the lysate obtained in d) is injected in the column, which is then washed with an eluent of high ionic strength. As an example, ammonium sulphate 1.5 M can be used. Since plasmid DNA possesses a weak hydrophobic character it does not bind to the support and is eluted firstly from the column. All the impurities contained in the lysate are more hydrophobic than the plasmid and thus interact with the hydrophobic support. As a consequence they are retarded during elution and exit the column separately from the plasmid. The plasmid DNA is then collected at the outlet of the column.

f) Concentration and/or buffer exchange: the plasmid DNA obtained in e) may be concentrated by addition of a precipitating agent such as isopropanol, ethanol or poly (ethylene glycol) under adequate concentration and conditions. The precipitated plasmid DNA is recovered as usual, by centrifugation or filtration, and re-dissolved in a smaller volume of a buffer adequate for its final use.

g) Preparation of a hydrophobic interaction chromatography support: a hydrophobic interaction chromatography support adequate for the purification of plasmid DNA according to the process described in e) is prepared by covalently coupling mildly hydrophobic molecules to an adequate solid support. This solid support may be any organic, inorganic or composite material, porous, super-porous (pore diameter $\geq 30$ μm) or nonporous, which is adequate for chromatography. As an example Sepharose CL-6B® can be used. The support mat be derivatized, for example, with poly(alkene glycols) (poly(propylene glycol), poly (ethylene glycol)), alkanes, alkenes, alkynes, aryls, 1,4-butanediol diglycidyl ether or other molecules which confer a hydrophobic character to the support.

Innovative Characteristics

The process developed possesses innovative characteristics, namely the use of non-commercial hydrophobic interaction chromatography solid supports to bind impurities contained in clarified cell lysates (RNA, denatured genomic DNA, denatured plasmid DNA, oligonucleotides, lipopolysaccharides), with the objective of purifying double stranded plasmid DNA.

EXAMPLE 1

Preparation of Pre-Purified Lysates Containing a Plasmid DNA with 8500 Base Pairs Cells of *Escherichia coli* (DH5α strain) were transformed with a plasmid with 8500 base pairs, and grown overnight at 37° C. in shake flasks containing LB (Luria Broth) culture medium, at an orbital stirring of 250 rpm. The cells were harvested at the end of the growth phase and separated by centrifugation at 18 000 g (15 minutes at 4° C.). The supernatant liquid was discarded. The cells were then lysed chemically in alkaline medium as described next. The cells corresponding to a culture medium of 500 ml were re-suspended in 25 ml of a solution with 61 mM glucose, 10 mM Tris buffer, pH 8.0 and 10 mM EDTA. The lysis was performed by addition of 25 ml of a pre-chilled (4–10° C.) solution with 200 mM of NaOH and 1% (w/v) of sodium dodecyl sulphate. The resulting solution was mixed gently and incubated on ice for 10 minutes. Next, the obtained lysate was neutralised by addition of 20 ml of a pre-chilled (4–10° C.) solution of potassium acetate 3 M, pH 5.0. The resulting solution was mixed gently and incubated on ice for 10 minutes. The precipitate formed (cell debris, genomic DNA and proteins) was removed by centrifugation at 18 000 g (20 min, 4° C.). The supernatant was filtered through paper filter in order to remove suspended particles. The total mass of plasmid DNA in this solution, measured by anion-exchange HPLC analysis was 3.9 mg.

The plasmid DNA contained in the clarified lysate (around 80 ml) was precipitated by the addition of 0.6 volumes of cold isopropanol (−20° C.). After mixing, the solution was incubated during 30 minutes at 4° C. The obtained precipitate was recovered by centrifugation at 10 000 g (20 min, 4° C.), and re-dissolved in 9 ml of Tris buffer 10 mM, pH 8.0. The total mass of plasmid DNA in this solution, measured by HPLC analysis, was 2.4 mg.

The plasmid DNA in this solution was pre-purified and conditioned by addition of solid ammonium sulphate up to a concentration of 2.5 M. The resulting solution was incubated during 15 minutes on ice. The precipitated proteins were removed by centrifugation at 10 000 g during 20 min. The total mass of plasmid DNA in the resulting supernatant, measured by HPLC analysis, was 1.8 mg, corresponding to a purity of 49%.

EXAMPLE 2

Preparation of Pre-Purified Lysates Containing a Plasmid DNA with 6050 Base Pairs Cells of *Escherichia coli* (DH5α strain) were transformed with a plasmid with 6050 base pairs, and grown overnight at 37° C. in shake flasks containing TB (Terrific Broth) culture medium, at an orbital stirring of 250 rpm. The cells were harvested at the end of the growth phase and separated by centrifugation at 18 000 g (15 minutes at 4° C.). The supernatant liquid was discarded. The cells were then lysed chemically in alkaline medium as described next. The cells corresponding to a culture medium of 500 ml were re-suspended in 25 ml of a solution with 61 mM glucose, 10 mM Tris buffer, pH 8.0 and 10 mM EDTA. The lysis was performed by addition of 25 ml of a pre-chilled (4–10° C.) solution with 200 mM of NaOH and 1% (w/v) of sodium dodecyl sulphate. The resulting solution was mixed gently and incubated on ice for 10 minutes. Next, the obtained lysate was neutralised by addition of 20 ml of a pre-chilled (4–10° C.) solution of potassium acetate 3 M, pH 5.0. The resulting solution was mixed gently and incubated on ice for 10 minutes. The precipitate formed (cell debris, genomic DNA and proteins) was removed by centrifugation at 18 000 g (20 min, 4° C.). The supernatant was filtered through paper filter in order to remove suspended particles. The total mass of plasmid DNA in this solution, measured by anion-exchange HPLC analysis was 8.7 mg.

The plasmid DNA contained in the clarified lysate (around 70 ml) was precipitated by the addition of 0.6 volumes of cold isopropanol (−20° C.). After mixing, the solution was incubated during 30 minutes at 4° C. The obtained precipitate was recovered by centrifugation at 10 000 g (20 min, 4° C.), and re-dissolved in 18 ml of Tris buffer 10 mM, pH 8.0. The total mass of plasmid DNA in this solution, measured by HPLC analysis, was 7.6 mg. The plasmid DNA in this solution was pre-purified and conditioned by addition of solid ammonium sulphate up to a concentration of 2.5 M. The resulting solution was incubated during 15 minutes on ice. The precipitated proteins were removed by centrifugation at 10 000 g during 20 min. The total mass of plasmid DNA in the resulting supernatant, measured by HPLC analysis, was 6 mg, corresponding to a purity of 32%.

EXAMPLE 3

Preparation of Pre-Purified Lysates Containing a Plasmid DNA with 7067 Base Pairs Cells of *Escherichia coli* (Top10F' strain) were transformed with a plasmid with 7067 base pairs, and grown overnight at 37° C. in a fermenter containing 4 liters of TB (Terrific Broth) culture medium. The cells were harvested at the end of the growth phase and separated by centrifugation at 14 300 g (15 minutes at 4° C.). The supernatant liquid was discarded. The cells were lysed chemically in alkaline medium as described next. The cells corresponding to a culture medium of 4000 ml were re-suspended in 75 ml of a solution with 50 mM glucose, 25 mM Tris buffer, pH 8.0 and 10 mM EDTA. The lysis was performed by addition of 75 ml of a pre-chilled (4–10° C.) solution with 200 mM of NaOH and 1% (w/v) of sodium dodecyl sulphate. The resulting solution was mixed gently and incubated on ice for 10 minutes. Next, the obtained lysate was neutralised by addition of 56 ml of a pre-chilled (4–10° C.) solution of potassium acetate 3 M, pH 5.0. The resulting solution was mixed gently and incubated on ice for 10 minutes. The precipitate formed (cell debris, genomic DNA and proteins) was removed by centrifugation at 14 300 g (25 min, 4° C.). The supernatant was filtered through paper filter in order to remove suspended particles. The total mass of plasmid DNA in this solution, measured by anion-exchange HPLC analysis was 86.5 mg.

The plasmid DNA contained in half of the volume of the clarified lysate (around 500 ml) was precipitated by the addition of 0.7 volumes of cold isopropanol (−20° C.). After mixing, the solution was incubated during 90 minutes at 4° C. The obtained precipitate was recovered by centrifugation at 10 000 g (30 min, 4° C.), and re-dissolved in 150 ml of Tris buffer 10 mM, pH 8.0. The total mass of plasmid DNA in this solution, measured by HPLC analysis, was 7.6 mg. The plasmid DNA in this solution was pre-purified and conditioned by addition of solid ammonium sulphate up to a concentration of 2.5 M. The resulting solution was incubated during 15 minutes on ice. The precipitated proteins were removed by centrifugation at 10 000 g during 20 min. The total mass of plasmid DNA in the resulting supernatant, measured by HPLC analysis, was 74.7 mg, corresponding to a purity of 66.1%.

EXAMPLE 4

Preparation of a Hydrophobic Interaction Chromatography Support by Derivatisation of Sepharose CL-6B® with 1,4-butanediol Diglycidyl Ether A non-commercial hydrophobic interaction chromatography support adequate for the purification of plasmid DNA was prepared as described next. The reagent 1,4-butanediol diglycidyl ether was covalently bound to a commercial, non-derivatised chromatographic support of Sepharose CL-6B®. Five grams of dry Sepharose CL-6B were washed with water in a Buchner funnel, and mixed with 5 ml of 1,4-butanediol diglycidyl ether. Five ml of a 0.6 M solution of sodium hydroxide containing 10 mg of sodium borohydride were added. The suspension was mixed by orbital shaking for 8 h at 25° C. The derivatization reaction was stopped by extensively washing the support with large volumes of distilled water in a Buchner funnel. The support was then treated with 1 M sodium hydroxide overnight at room temperature, for the purpose of inactivating free epoxy groups.

EXAMPLE 5

Preparation of a Hydrophobic Interaction Chromatography Support by Derivatisation of Sepharose CL-6B® with Poly(Propylene Glycol) 380

A non-commercial hydrophobic interaction chromatography support adequate for the purification of plasmid DNA was prepared as described next. The reagent diglycidyl ether of poly(propylene glycol) 380 was covalently bound to a commercial, non-derivatised support of Sepharose CL-6B®. Five grams of dry Sepharose CL-6B were washed with water in a Buchner funnel, and mixed with 5 ml of diglycidyl ether of poly(propylene glycol) 380. Five ml of a 0.6 M solution of sodium hydroxide containing 10 mg of sodium borohydride were added. The suspension was mixed by orbital shaking for 8 h at 25° C. The derivatization reaction was stopped by extensively washing the support with large volumes of distilled water in a Buchner funnel. The support was then treated with 1 M sodium hydroxide overnight at room temperature, for the purpose of inactivating free epoxy groups.

EXAMPLE 6

Hydrophobic Interaction Chromatography with a Non-Commercial Support

Figure 2:
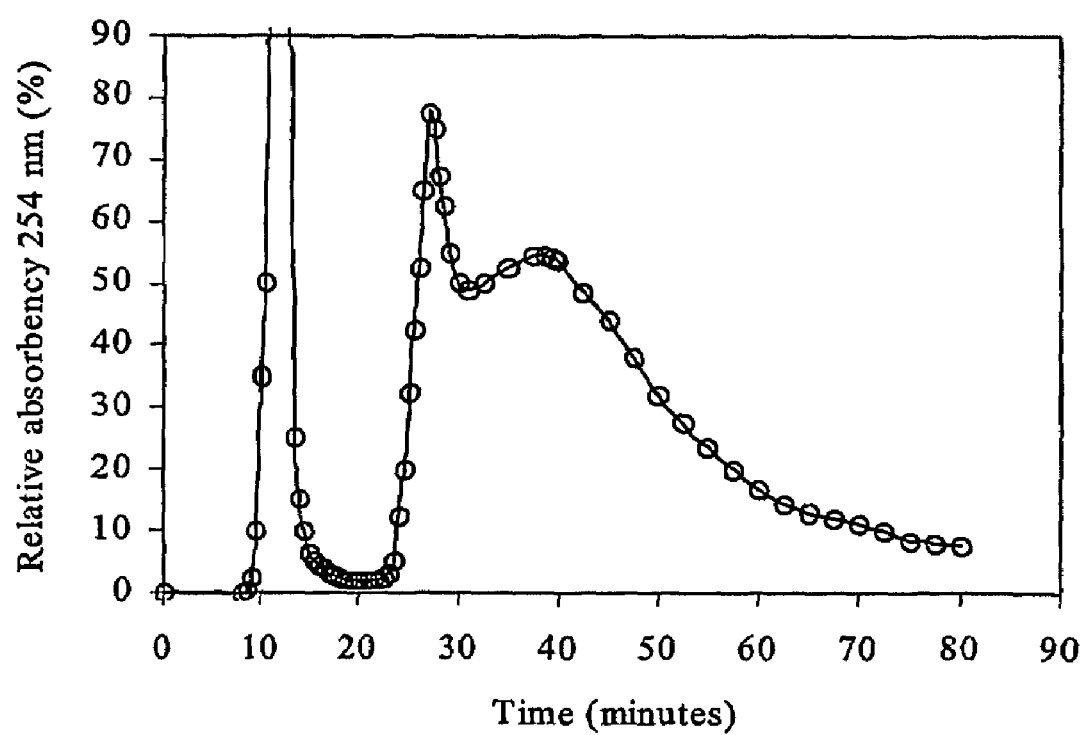
FIG. 2 is a hydrophobic interaction chromatography chromatogram of $E.\ coli$ (DH5α) (25 µg of plasmid DNA) using a Sepharose CL-6B® modified with 1,4-butanediol diglycidyl ether support. Elution was performed at a flow rate of 1 ml/mm with a 1.5 M solution of ammonium sulphate in 10 mM Tris, pH 8.0.

A glass column XK 16/20 (20 cm×1.6 cm) from Pharmacia was packed with 28 ml of the hydrophobic interaction chromatography support (Sepharose CL-6B® modified with 1,4-butanediol diglycidyl ether) prepared as described in Example 4. A chromatographic bed with 14 cm height was obtained. The column was connected to the medium-pressure liquid chromatography system from Pharmacia, Fast Protein Liquid Chromatography (FPLC). The column was equilibrated with a 1.5 M solution of ammonium sulphate in 10 mM Tris, pH 8.0 at a flow rate of 1 ml/min. Five hundred µl of the plasmid DNA solution (25 µg of plasmid DNA) pre-purified and conditioned as described in Example 1 were injected in the column. Elution was performed at a flow rate of 1 ml/min with a 1.5 M solution of ammonium sulphate in 10 mM Tris, pH 8.0. The absorbency of the eluate was continuously measured at the column outlet at 254 nm. One-ml fractions were collected in 1.5 ml tubes. After elution of the species which do not interact with the support (plasmid DNA) and of the species which interact moderately (denatured genomic DNA, denatured plasmid DNA, RNA and oligonucleotides), the elution was continued at 1 ml/min with a solution of 10 mM Tris. pH 8.0 in order to remove the species which bind to the support (lipopolysaccharides). The column was finally washed with a 1 M solution of sodium hydroxide, and re-equilibrated at a flow rate of 1 ml/min with a 1.5 M solution of ammonium sulphate in 10 mM Tris, pH 8.0. FIG. 2 presents the chromatogram obtained. The first peak, which elutes at 10 minutes, contains plasmid DNA. The species that interact moderately (denatured genomic DNA, denatured plasmid DNA, RNA, oligonucleotides and lipopolysaccharides) elute from 23 minutes on as a broad peak.

The fractions containing plasmid DNA were pooled and analysed by means of different analytical techniques: HPLC, agarose gel electrophoresis, restriction analysis, transformation experiments, Southern analysis, endotoxin analysis (LAL method) and protein analysis. The plasmid DNA mass was measured by HPLC analysis: the yield of chromatography was determined to be 70% and the HPLC purity was higher than 99%. The identity of the plasmid was confirmed by restriction analysis using restriction enzymes in accordance with the plasmid restriction map. The absence of RNA and of denatured plasmid forms was demonstrated by anion exchange HPLC and agarose gel electrophoresis. The absence of proteins in the final plasmid DNA solution was demonstrated by protein analysis using the Pierce method and polyacrylamide gel electrophoresis. The levels of contamination by genomic DNA were assessed by Southern analysis, which determined a residual amount of *Escherichia coli* genomic DNA between 3 and 6.2 ng/µg of plasmid DNA. This value is bellow the levels required for plasmid DNA preparations to be used in gene therapy (<10 ng/µg of plasmid DNA). The endotoxin levels were measured by the LAL method to be equal to 0.048 EU/µg of plasmid DNA. This value is bellow the levels required for plasmid DNA preparations to be used in gene therapy (<0.1 EU/µg of plasmid DNA). The purified plasmid DNA was used to transform competent cells of DH5α. The transformation efficiency calculated was similar to the one obtained using plasmid DNA purified by alternative methods.

EXAMPLE 7

Hydrophobic Interaction Chromatography with a Commercial Support

Figure 3:
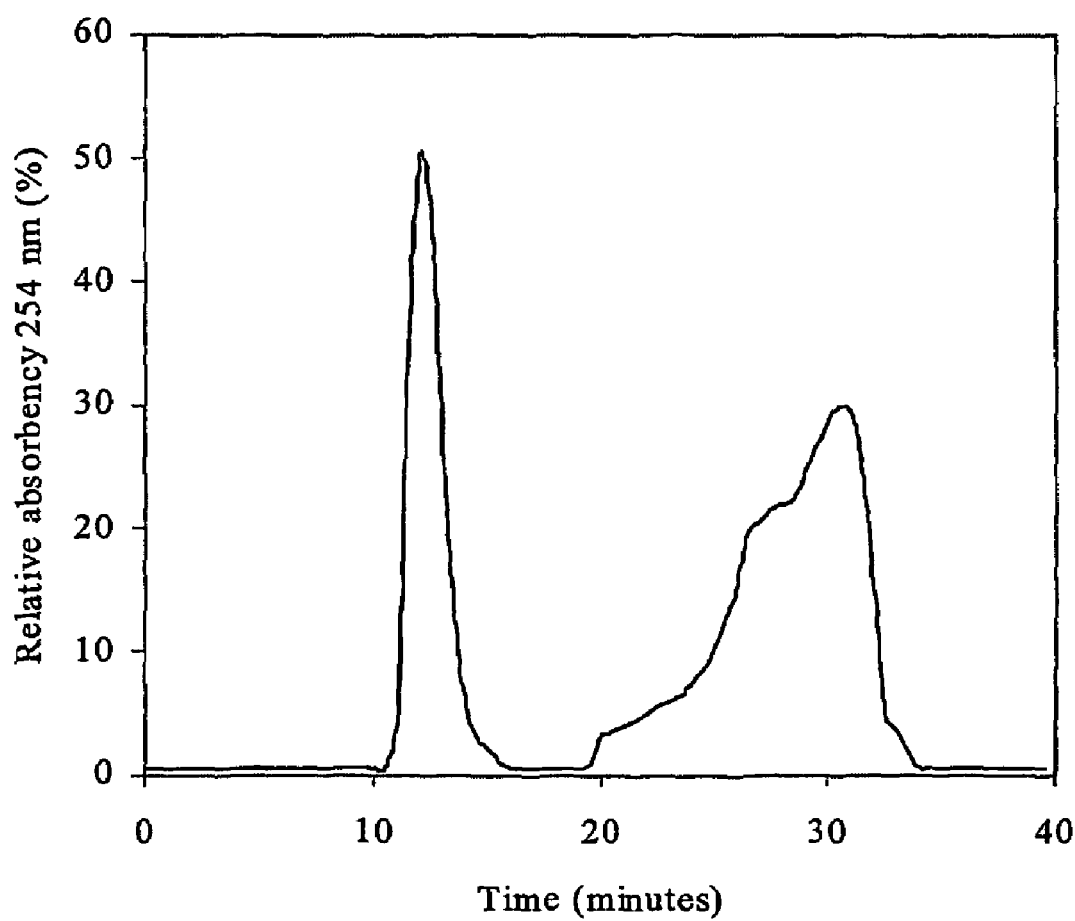
FIG. 3 is a hydrophobic interaction chromatography chromatogram of $E.\ coli$ (DH5α) (149 µg of plasmid DNA) using a Phenyl-Sepharose support. Elution was performed at a flow rate of 1 ml/min with a 1.5 M solution of ammonium sulphate in 10 mM Tris, pH 8.0.

A glass column XK 16/20 (20 cm×1.6 cm) from Pharmacia was packed with 28 ml of the hydrophobic interaction chromatography support Phenyl-Sepharose from Pharmacia. A chromatographic bed with 14 cm height was obtained. The column was connected to the medium-pressure liquid chromatography system from Pharmacia, Fast Protein Liquid Chromatography (FPLC). The column was equilibrated at a flow rate of 1 ml/min with a 1.5 M solution of ammonium sulphate in 10 mM Tris, pH 8.0. Five hundred µl of the plasmid DNA solution (149 µg of plasmid DNA) pre-purified and conditioned as described in Example 2 were injected in the column. Elution was performed at a flow rate of 1 ml/min with a 1.5 M solution of ammonium sulphate in 10 mM Tris, pH 8.0. The absorbency of the eluate was continuously measured at the column outlet at 254 nm. One-ml fractions were collected in 1.5 ml tubes. After elution of the species which do not interact with the support (plasmid DNA), the elution was continued at 1 ml/min with a solution of 10 mM Tris, pH 8.0 in order to remove the species which interact moderately (denatured genomic DNA, denatured plasmid DNA, RNA and oligonucleotides) and the species which bind to the support (lipopolysaccharides). The column was finally washed with a 1 M solution of sodium hydroxide, and re-equilibrated at a flow rate of 1 ml/min with a 1.5 M solution of ammonium sulphate in 10 mM Tris, pH 8.0. FIG. 3 presents the chromatogram obtained. The first peak, which elutes at 10 minutes, contains plasmid DNA. The species that interact moderately (denatured genomic DNA, denatured plasmid DNA, RNA, oligonucleotides and lipopolysaccharides) elute from 20 minutes on as a broad peak.

The fractions containing plasmid DNA were pooled and analysed by means of different analytical techniques: HPLC, agarose gel electrophoresis, restriction analysis, transformation experiments, Southern analysis, endotoxin analysis (LAL method) and protein analysis. The plasmid DNA mass was measured by HPLC analysis: the yield of chromatography was determined to be 85% and the HPLC purity was higher than 99%. The identity of the plasmid was confirmed by restriction analysis using restriction enzymes in accordance with the plasmid restriction map. The absence of RNA and of denatured plasmid forms was demonstrated by anion exchange HPLC and agarose gel electrophoresis. The absence of proteins in the final plasmid DNA solution was demonstrated by protein analysis using the Pierce method and polyacrylamide gel electrophoresis. The purified plasmid DNA was used to transform competent cells of DH5α. The efficiency of transformation calculated was similar to the one obtained using plasmid DNA purified by alternative methods.

EXAMPLE 8

Scale-Up of Hydrophobic Interaction Chromatography

Figure 4:
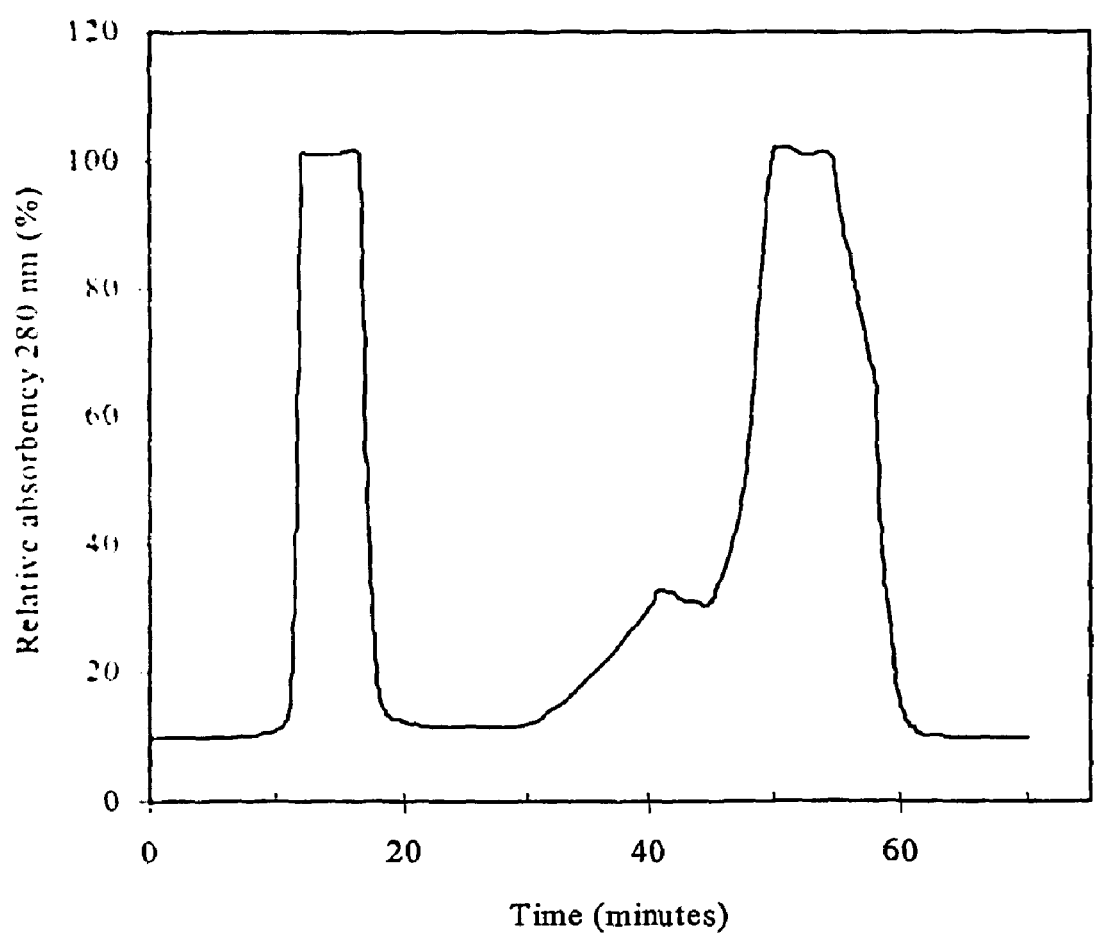
FIG. 4 is a hydrophobic interaction chromatography chromatogram of $E.\ coli$ (Top10F') (14942 µg of plasmid DNA) using a Sepharose CL-6B® with poly(propylene glycol) 380 support. Elution was performed at a flow rate of 10 ml/mm with a 1.5 M solution of ammonium sulphate in 10 mM Tris, pH 8.0.

This example shows that the purification of plasmid DNA by hydrophobic interaction chromatography can be performed at larger scales without significant impact on the quality of the final product. A glass column XK 50/30 (30 cm×5 cm) from Pharmacia was packed with 334 ml of the hydrophobic interaction chromatography support prepared as described in Example 5 (Sepharose CL-6B® with poly (propylene glycol) 380). A chromatographic bed with 17 cm height was obtained. The column was connected to the medium-pressure liquid chromatography system Biopilot from Pharmacia, and equilibrated at a flow rate of 10 ml/min with a 1.5 M solution of ammonium sulphate in 10 mM Tris, pH 8.0. Thirty ml of the plasmid DNA solution (14942 μg of plasmid DNA) pre-purified and conditioned as described in Example 3 were injected in the column. Elution was performed at a flow rate of 10 ml/min with a 1.5 M solution of ammonium sulphate in 10 mM Tris, pH 8.0. The absorbency of the eluate was continuously measured at the outlet at 280 nm. Fractions were collected at the column outlet. After elution of the species which do not interact with the support (plasmid DNA) and of the species which interact moderately (denatured genomic DNA, denatured plasmid DNA, RNA and oligonucleotides), the elution was continued at 10 ml/min with a solution of 10 mM tris, pH 8.0 in order to remove and the species which bind to the support (lipopolysaccharides). The column was finally washed with a 1 M solution of sodium hydroxide, and re-equilibrated at a flow rate of 10 ml/min with a 1.5 M solution of ammonium sulphate in 10 mM Tris, pH 8.0. FIG. 4 presents the chromatogram obtained. The first peak, which elutes at 10 minutes, contains plasmid DNA. The species that interact moderately (denatured genomic DNA, denatured plasmid DNA, RNA, oligonucleotides and lipopolysaccharides) elute from 30 minutes on as a broad peak.

The fractions containing plasmid DNA were pooled and analysed by means of different analytical techniques: HPLC, agarose gel electrophoresis, restriction analysis, transformation experiments, Southern analysis, endotoxin analysis (LAL method) and protein analysis. The volume of the plasmid fraction was of 77 ml. The plasmid DNA mass was measured by HPLC analysis: the yield of chromatography was determined to be 95%, the plasmid concentration was 184 mg/ml, and the HPLC purity was higher than 99%. The identity of the plasmid was confirmed by restriction analysis using restriction enzymes in accordance with the plasmid restriction map. The absence of RNA and of denatured plasmid forms was demonstrated by anion exchange HPLC and agarose gel electrophoresis. The absence of proteins in the final plasmid DNA solution was demonstrated by protein analysis using the Pierce method and polyacrylamide gel electrophoresis. The levels of contamination by genomic DNA were assessed by Southern analysis, which determined a residual amount of *Escherichia coli* genomic DNA lower than 7.8 ng/μg of plasmid DNA. This value is bellow the levels required for plasmid DNA preparations to be used in gene therapy (<10 ng/μg of plasmid DNA). The endotoxin levels were measured by the LAL method to be equal to 0.00026 EU/μg of plasmid DNA. This value is bellow the levels required for plasmid DNA preparations to be used in gene therapy (<0.1 EU/μg of plasmid DNA). The purified plasmid DNA was used to transform competent cells of DH5α. The efficiency of transformation calculated was similar to the one obtained using plasmid DNA purified by alternative methods.

EXAMPLE 9

Separation of Denatured Plasmid DNA by Hydrophobic Interaction Chromatography

This example shows that hydrophobic interaction chromatography is capable of separating native forms of plasmid DNA from denatured forms. The term denatured refers to conformations of plasmid DNA in which the hydrogen bonds between complementary strands are disrupted. These denatured forms originate essentially during the alkaline lysis process, especially if the pH of the lysis mixtures exceeds the value of 12.5. The term native refers to conformations of plasmid DNA in which the hydrogen bonds between complementary strands are intact.

Figure 5:
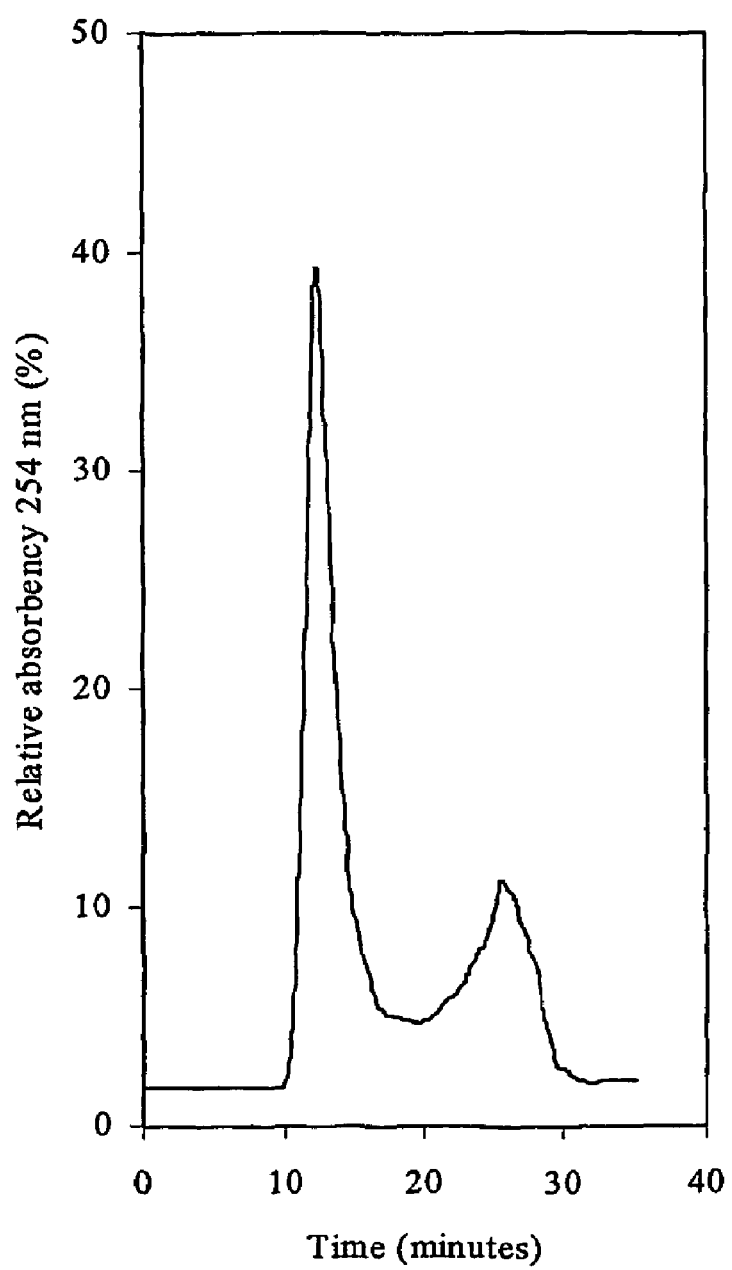
FIG. 5 is a hydrophobic interaction chromatography chromatogram, separating native plasmid DNA from denatured plasmid DNA (500 µg, 22 µg) using Sepharose CL-6B® modified with 1,4-butanediol diglycidyl ether support. Elution was performed at a flow rate of 1 ml/min wit a 1.5 M solution of ammonium sulphate in 10 mM Tris, pH 8.0.

Mixtures containing native and denatured plasmid DNA were artificially prepared as described next. Pure plasmid DNA, obtained as described in Example 6, was denatured by controlled incubation at 75° C. in the presence of 133 mM NaOH. Thus it was possible to prepare samples containing different amounts of native and denatured plasmid DNA. Next, a glass column XK 16/20 (20 cm×1.6 cm) from Pharmacia was packed with 28 ml of the hydrophobic interaction chromatography support (Sepharose CL-6B® modified with 1,4-butanediol diglycidyl ether) prepared as described in Example 4. A chromatographic bed with 14 cm height was obtained. The column was connected to the medium-pressure liquid chromatography system from Pharmacia, Fast Protein Liquid Chromatography (FPLC) and equilibrated at a flow rate of 1 ml/min with a 1.5 M solution of ammonium sulphate in 10 mM Tris, pH 8.0. Samples of plasmid DNA prepared by artificial denaturation were then injected (500 μl, 22 μg/ml). Elution was performed at a flow rate of 1 ml/min with a 1.5 M solution of ammonium sulphate in 10 mM Tris, pH 8.0. The absorbency of the eluate was continuously measured at the outlet at 254 nm. One-ml fractions were collected in 1.5 ml tubes. FIG. 5 shows the chromatogram obtained. The native plasmid DNA does not interact with the support, and elutes from 10 minutes on. The denatured plasmid DNA interacts moderately with the support and elutes from 20 minutes on. This way, the hydrophobic interaction column proposed enables the separation of native plasmid DNA from denatured plasmid DNA. The material in each peak was collected separately and identification tests were carried using restriction enzymes and agarose gel electrophoresis.

REFERENCES

Birnboim, H. C., Doly, J. 1979. The rapid alkaline extraction procedure for screening recombinant plasmid DNA. Nucleic Acids Res. 7: 1513–1523.

Diogo, M. M., Queiroz, J. A., Monteiro, G. A., Prazeres, D. M. F. 1999. Separation and analysis of denatured plasmid forms using hydrophobic interaction chromatography. Anal. Biochem. 275: 122–124.

Diogo, M. M., Queiroz, J. A., Monteiro, G. A., Martins, S. A. M., Ferreira, G. N. M., Prazeres, D. M. F. 2000. Purification of the cystic fibrosis plasmid vector for gene therapy using hydrophobic interaction chromatography, Biotechnol. Bioeng., 68: 576–583.

Diogo, M. M., Silva, S., Cabral, J. M. S., Queiroz, J. A., 1999. Hydrophobic interaction chromatography of *Chromobacterium viscosum* lipase on polypropylene glycol immobilized on sepharose. J. Chromatogr. The 849: 413–419.

Ferreira, G. N. M., Cabral, J. M. S., Prazeres, D. M. F. 1999a. Monitoring of plasmid DNA production and purification for gene therapy applications. Pharmacy Pharmac. Commun. 5: 57–59.

Ferreira, G. N. M., Cabral, J. M. S., Prazeres, D. M. F. 1999b. Development of process flow sheets for the purification of supercoiled plasmids for gene therapy applications. Biotechnol. Progress, 15(4): 725–731.

Green, A. P., Prior, G. M., Helveston, N. M., Taittinger, B. E., Liu, X., Thompson, J. A. 1997. Preparative purification of supercoiled plasmid DNA for therapeutic applications. Biopharm, May: 52–62.

Horn, N. A., Meek, J. A., Budahazi, G., Marquet, M. 1995. Cancer gene therapy using plasmid DNA: Purification of DNA for human clinical trials. Hum. Gene Ther. 6: 565–573.

Prazeres, D. M. F., Monteiro, G. A., Ferreira, G. N. M., Cooney, C. L., Cabral, J. M. S. 1999. Large-scale production of pharmaceutical-grade plasmid DNA for gene therapy: problems and bottlenecks. Trends Biotechnol. 17: 169–174.

Prazeres D. M. F., Schluep, T., Cooney, C. 1998. Preparative purification of supercoiled plasmid DNA using anion-exchange chromatography. J. Chromatogr. The 806: 31–45.

Queiroz J. A. Garcia, F. A. P., Cabral, J. M. S. 1995. Hydrophobic interaction chromatography of *Chromobacterium viscosum* lipase. J. Chromatogr. The 707: 137–142.

Queiroz. J. A., Garcia, F. A. P., Cabral, J. M. S. 1996. Hydrophobic interaction chromatography of *Chromobacterium viscosum* lipase on polyetylhene glycol immobilized on sepharose. J. Chromatogr. The 734: 213–219.

Sambrook, J., Fritisch, E. F., Maniatis, T. 1989. Molecular Cloning: Laboratory Manual, 2nd ed, Cold Spring Harbor Laboratory Press, New York.

Schleef, M. 1999. Issues of large-scale plasmid DNA manufacturing, pp 443–469.

In: H.-J- Rehm and G. Reed (eds.), Biotechnology, Volume 5a, Wiley-VCH, Weinheim.

Schluep. T., Cooney, C. L. 1998. Purification of plasmids by triplex affinity interaction. Nucleic Acids Res. 26: 4524–4528.

Sundberg. L., Porath J. 1974. Preparation of adsorbents for biospecific affinity chromatography. I. Attachment of group-containing ligands to insoluble polymers by means of bifunctional oxiranes. J. Chromatogr. 90: 87–98.

US Food and Drug Administration 1996. Addendum to the points to consider in human somatic cell and gene therapy. US Food and Drug Administration, Rockville, Md., USA.

Patents

Marquet et al., U.S. Pat. No. 5,561,064, October/1996

Horn et al., U.S. Pat. No. 5,707,812, January/1998

Yamamoto, U.S. Pat. No. 5,843,731, December/1998

What is claimed is:

1. A process for the production and purification of pharmaceutical-grade plasmid DNA comprising:
   a) production of cells containing plasmid DNA,
   b) preparation of a lysate containing plasmid DNA by disrupting cells wit the method of alkaline lysis,
   c) a concentration step by precipitation with an adequate agent,
   d) a pre-purification and conditioning step by addition of a salt,
   e) a hydrophobic interaction chromatography purification, and
   f) a final step of concentration and/or buffer exchange.

2. The process of claim 1, wherein the preparation of the lysate further comprises mechanical lysis.

3. The process of claim 1, wherein the concentration step by precipitation is performed with isopropanol or with poly(ethylene glycol) with an average molecular weight between 7000 and 9000.

4. The process of claim 1, wherein the pre-purification and conditioning step by salt addition is made with ammonium sulphate in the concentration range of 1.5 to 3.5 M.

5. The process of claim 1, which further comprises a step of sterilization formulation and filling of vials with the purified plasmid DNA.

6. The process of according to claim 1, wherein the process is used to purify and separate DNA on a preparative or analytical scale, which is then to be used in gene therapy, DNA vaccination or research applications.

7. A process for hydrophobic interaction chromatography for the purification of plasmid or genomic DNA contained in clarified lysates obtained from cells, the clarified lysates further containing impurities, wherein the process comprises:
   contacting the clarified lysates with a hydrophobic solid support,
   eluting the plasmid or genomic DNA from the solid support, wherein the plasmid or genomic DNA elutes before the impurities.

8. The process of claim 7, wherein the solid support is any organic, inorganic or composite material, porous, superporous or non-porous, suitable for chromatographic separations, which is derivatized with poly(alkene glycols), alkanes, alkenes, alkynes, arenes or other molecules that confer a hydrophobic character to the support or combinations thereof.

9. The process of hydrophobic interaction chromatography of claim 7, wherein the solid support comprises agarose, wherein the agarose is derivatized with poly(propylene glycol), poly(ethylene glycol) or 1,4-butanediol diglycidyl ether.

10. The process of claim 7, wherein the process is used to purify double stranded genomic DNA contained in the clarified lysates prepared from cells.

11. The process of claim 7, wherein it is used to separate denatured plasmid DNA from native plasmid DNA contained in clarified or pre-purified lysates, prepared from cells.

12. The process of claim 7, wherein the purification by hydrophobic interaction chromatography is carried out in a fixed bed.

13. The process of claim 7, wherein the purification by hydrophobic interaction chromatography is carried out in an expanded bed.

14. The process of claim 7, wherein it is used to purify and separate DNA at a preparative or analytical scale, which is then to be used in gene therapy, DNA vaccination or research applications.

15. The process of claim 7, wherein the impurities are proteins, denatured genomic DNA, RNA, oligoribonucleotides, oligodeoxyribonocleotides, denatured plasmid DNA or lipopolysaccharides.

* * * * *

UNITED STATES PATENT AND TRADEMARK OFFICE
CERTIFICATE OF CORRECTION

PATENT NO. : 7,169,917 B2
APPLICATION NO. : 10/332633
DATED : January 30, 2007
INVENTOR(S) : de Franca Teixeira dos Prazeres et al.

It is certified that error appears in the above-identified patent and that said Letters Patent is hereby corrected as shown below:

Col. 12, line 14, claim 1: "cells wit the method" should read --cells with the method--

Signed and Sealed this

Twenty-sixth Day of June, 2007

JON W. DUDAS
*Director of the United States Patent and Trademark Office*